United States Patent
Naitou et al.

(10) Patent No.: US 7,662,742 B2
(45) Date of Patent: Feb. 16, 2010

(54) PROCESS FOR PRODUCING CATALYST FOR METHACRYLIC ACID PRODUCTION, CATALYST FOR METHACRYLIC ACID PRODUCTION, AND PROCESS FOR PRODUCING METHACRYLIC ACID

(75) Inventors: Hiroyuki Naitou, Otake (JP); Takashi Karasuda, Otake (JP); Tomoki Fukui, Otake (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 202 days.

(21) Appl. No.: 10/577,136

(22) PCT Filed: Oct. 27, 2004

(86) PCT No.: PCT/JP2004/015893

§ 371 (c)(1),
(2), (4) Date: Apr. 25, 2006

(87) PCT Pub. No.: WO2005/039760

PCT Pub. Date: May 6, 2005

(65) Prior Publication Data
US 2007/0032679 A1    Feb. 8, 2007

(30) Foreign Application Priority Data
Oct. 27, 2003  (JP)  ............................ 2003-365984

(51) Int. Cl.
| | | |
|---|---|---|
| B01J 27/00 | (2006.01) | |
| B01J 27/198 | (2006.01) | |
| B01J 27/188 | (2006.01) | |
| B01J 27/19 | (2006.01) | |
| B01J 27/192 | (2006.01) | |
| B01J 27/185 | (2006.01) | |
| B01J 23/00 | (2006.01) | |
| B01J 23/32 | (2006.01) | |
| B01J 23/02 | (2006.01) | |
| B01J 23/04 | (2006.01) | |
| B01J 23/70 | (2006.01) | |
| B01J 23/72 | (2006.01) | |
| B01J 23/08 | (2006.01) | |

(52) U.S. Cl. .................. 502/208; 502/209; 502/210; 502/211; 502/212; 502/213; 502/305; 502/308; 502/311; 502/317; 502/319; 502/321; 502/324; 502/325; 502/344; 502/345; 502/353; 502/355

(58) Field of Classification Search .............. None
See application file for complete search history.

(56) References Cited

U.S. PATENT DOCUMENTS

2006/0041168 A1 *   2/2006   Naitou et al. ............... 562/535

FOREIGN PATENT DOCUMENTS

| JP | 05-031368 | 2/1993 |
|---|---|---|
| JP | 10-244160 | 9/1998 |
| JP | 11-226412 | 8/1999 |
| JP | 2000-024502 | 1/2000 |
| JP | 2000-296336 | 10/2000 |
| JP | 2000296336 | * 10/2000 |
| JP | 2002-292291 | 10/2002 |
| JP | 2003-154273 | 5/2003 |
| JP | 2003-190798 | 7/2003 |
| JP | 2004-008834 | 1/2004 |
| JP | 2004-268027 | 9/2004 |
| WO | 00/72964 | 12/2000 |

OTHER PUBLICATIONS

U.S. Appl. No. 11/631,107, filed Dec. 28, 2006, Fukui, et al.

* cited by examiner

Primary Examiner—Karl J Puttlitz
(74) Attorney, Agent, or Firm—Oblon, Spivak, McClelland, Maier & Neustadt, L.L.P.

(57) ABSTRACT

A method for producing a catalyst containing given atoms in a given atomic proportion for use in producing methacrylic acid through gas-phase catalytic oxidation of methacrolein with molecular oxygen comprising the steps of:

(i) preparing a solution or slurry containing at least molybdenum, phosphorus, and vanadium (liquid I);

(ii) preparing a solution or slurry containing ammonium radical (liquid II);

(iii) preparing a mixture of the liquid I and the liquid II by introducing one liquid (liquid PR) of the liquid I and the liquid II into a tank (tank A) and pouring the other liquid (liquid LA) on a continuous region in the surface of the liquid PR, the continuous region occupying 0.01 to 10% of the whole area of the surface of the liquid PR; and (iv) drying and calcining the resultant solution or slurry containing a catalyst precursor comprising all the catalyst constituents.

3 Claims, No Drawings

PROCESS FOR PRODUCING CATALYST FOR METHACRYLIC ACID PRODUCTION, CATALYST FOR METHACRYLIC ACID PRODUCTION, AND PROCESS FOR PRODUCING METHACRYLIC ACID

TECHNICAL FIELD

The present invention relates to a method for producing a catalyst for use in producing methacrylic acid (hereinafter, in some cases expressed as methacrylic acid production catalyst) through gas-phase catalytic oxidation of methacrolein with molecular oxygen, a catalyst for producing methacrylic acid, and a method for producing methacrylic acid.

BACKGROUND ART

In Patent document 1, a method for preparing a catalyst is disclosed, wherein a homogeneous solution containing at least one element selected from molybdenum, vanadium, phosphorous, antimony, copper and the like, a homogeneous solution containing at least one element selected from potassium, rubidium, cesium and thallium, a homogeneous solution containing at least one element selected from tungsten, beryllium, magnesium and the like, and ammonia if necessary are mixed and the resultant product is dried to obtain the catalyst.

Further, in Patent document 2, a method for producing a catalyst for use in producing methacrylic acid is disclosed, wherein the following step is included in which a solution or slurry containing at least molybdenum, phosphorous and vanadium and a solution or slurry containing ammonium compound are mixed and to the resultant solution or slurry a solution or slurry containing potassium and the like is added. Especially, an embodiment is disclosed in which ammonia water is dropped in a solution containing molybdenum, phosphorus and vanadium to mix both solutions.

Patent document 1: Japanese Patent Application, First Publication No. Hei 5-31368
Patent document 2: Japanese Patent Application, First Publication No. 2000-296336

DISCLOSURE OF INVENTION

Problem to be Solved by the Invention

However, the catalysts produced by using the methods disclosed in these patent documents didn't always realize a sufficient yield of methacrylic acid and, and hence an industrial catalyst with a superior performance has been desired.

The objects of the present invention are to provide a catalyst for producing methacrylic acid with a high yield, a method for producing the catalyst and a method for producing methacrylic acid by using the catalyst.

Means for Solving Problem

A method for producing methacrylic acid production catalyst of the present invention, which has solved the aforementioned problem, is
a method for producing a catalyst having a composition represented by the following formula (1) for use in producing methacrylic acid through gas-phase catalytic oxidation of methacrolein with molecular oxygen, comprising the steps of:

(i) preparing a solution or slurry containing at least molybdenum, phosphorus, and vanadium (liquid I);

(ii) preparing a solution or slurry containing ammonium radical (liquid II);

(iii) preparing a mixture of the liquid I and the liquid II by introducing one liquid (liquid PR) of the liquid I and the liquid II into a tank (tank A) and pouring the other liquid (liquid LA) on a continuous region in the surface of the liquid PR, the continuous region occupying 0.01 to 10% of the whole area of the surface of the liquid PR; and (iv) drying and calcining the resultant solution or slurry containing a catalyst precursor comprising all the aforementioned catalyst constituents.

$$P_aMo_bV_cCu_dX_eY_fZ_gO_h \qquad (1)$$

In the aforementioned formula (1), P, Mo, V, Cu and O represent phosphorous, molybdenum, vanadium, copper and oxygen, respectively; X represents at least one element selected from the group consisting of antimony, bismuth, arsenic, germanium, zirconium, tellurium, silver, selenium, silicon, tungsten and boron; Y represents at least one element selected from the group consisting of iron, zinc, chromium, magnesium, tantalum, cobalt, manganese, barium, gallium, cerium and lanthanum; Z represents at least one element selected from the group consisting of potassium, rubidium and cesium; and in the formula (1), subscripts a, b, c, d, e, f, g and h represent an atomic ratio of each element, respectively; when b is 12, a is in the range of from 0.5 to 3, c is in the range of from 0.01 to 3, d is in the range of from 0.01 to 2, e is in the range of from 0 to 3, f is in the range of from 0 to 3, g is in the range of from 0.01 to 3 and h represents the atomic ratio of oxygen necessary for fulfilling the requirement of the valence of each element above.

Further, the method for producing methacrylic acid production catalyst of the present invention is characterized in that the aforementioned liquid LA is poured while stirring the liquid PR introduced into the aforementioned tank A with a stirring power of 0.01 to 3.5 kW/m³.

Further, the method for producing methacrylic acid production catalyst of the present invention is characterized in that the aforementioned liquid LA is poured from the height of 0.05 to 2 m above the surface of the liquid PR introduced into the aforementioned tank A.

Further, the present invention in which the aforementioned problem has been solved resides in the catalyst produced according to the aforementioned method of the present invention.

Further, the present invention in which the aforementioned problem has been solved also resides in a method for producing methacrylic acid through gas-phase catalytic oxidation of methacrolein with molecular oxygen in the presence of methacrylic acid production catalyst of the present invention.

EFFECT OF THE INVENTION

According to the present invention, it is possible to provide a method for producing a catalyst for use in producing methacrylic acid through gas-phase catalytic oxidation of methacrolein with molecular oxygen, a catalyst with a high yield of methacrylic acid and a method for producing methacrylic acid by which methacrylic acid can be produced in a high yield.

BEST MODE FOR CARRYING OUT THE INVENTION

The methacrylic acid production catalyst, which can be produced by the method of the present invention, is used when methacrylic acid is produced through gas-phase catalytic oxidation of methacrolein with molecular oxygen and has a composition represented by the following formula (1).

 (1)

In the formula (1), P, Mo, V, Cu and O represent phosphorous, molybdenum, vanadium, copper and oxygen, respectively; X represents at least one element selected from the group consisting of antimony, bismuth, arsenic, germanium, zirconium, tellurium, silver, selenium, silicon, tungsten and boron; Y represents at least one element selected from the group consisting of iron, zinc, chromium, magnesium, tantalum, cobalt, manganese, barium, gallium, cerium and lanthanum; Z represents at least one element selected from the group consisting of potassium, rubidium and cesium; and subscripts a, b, c, d, e, f, g and h represent an atomic ratio of each element, respectively; when b is 12, a is in the range of from 0.5 to 3, c is in the range of from 0.01 to 3, d is in the range of from 0.01 to 2, e is in the range of from 0 to 3, f is in the range of from 0 to 3, g is in the range of from 0.01 to 3 and h represents the atomic ratio of oxygen necessary for fulfilling the requirement of the valence of each element above.

The method for producing methacrylic acid production catalyst of the present invention comprises the steps of:

(i) preparing a solution or slurry containing at least molybdenum, phosphorus, and vanadium (liquid I);

(ii) preparing a solution or slurry containing ammonium radical (liquid II);

(iii) preparing a mixture of the liquid I and the liquid II by introducing one liquid (in some cases expressed as liquid PR) of the liquid I and the liquid II into a tank (in some cases expressed as tank A) and pouring the other liquid (in some cases expressed as liquid LA) on a continuous region in the surface of the liquid PR, the continuous region occupying 0.01 to 10% of the whole area of the surface of the liquid PR; and (iv) drying the resultant solution or slurry containing a catalyst precursor comprising all the aforementioned catalyst constituents and calcining the resultant dried catalyst precursor (in some cases "drying the resultant solution . . . catalyst constituents and calcining the resultant dried catalyst precursor" is expressed as "drying and calcining the resultant dried catalyst precursor").

The ammonium radical in the present invention represents ammonia ($NH_3$) which can be changed into ammonium ($NH_4^+$) or ammonium which is included in ammonium compounds such as ammonium salts.

In the present invention, a tank to be used for preparing the liquid I and the liquid II and the tank A to be used for mixing both liquids are not particularly limited and a conventionally known tank can be used, however, a vessel type reactor can be preferably used. Moreover, the tank may be equipped with a stirrer, a baffle board and a jacket or a coil for heat exchanging. The stirrer may be equipped with a publicly known mixing blade such as a paddle blade, a propeller blade, a turbine blade, a flat blade, a bent blade or the like in one stage or in two or more stages in the vertical direction of the stirrer. The stirrer may be equipped with the same type or different types of blades. Further, a stirrer which is equipped with blade that is called large blade such as screw anchor or "MAX-BLEND" (registered trade name, manufactured by Sumitomo Heavy Industries, Ltd.) can be used.

Hereinafter, a preparing method of the liquid I and the liquid II and a mixing method of both liquids are described in detail.

<Preparing Method of the Liquid I>

The liquid I is prepared by dissolving or suspending raw materials such as compounds of at least molybdenum, phosphorus and vanadium in the solvent. The liquid I may contain compounds of copper, the aforementioned element X, the aforementioned element Y, the aforementioned element Z, and compounds containing ammonium radical as well as molybdenum, phosphorus and vanadium.

The amount of ammonium radical contained in the liquid I is not particularly limited, it is preferably 0 to 1.5 mols per 12 mols of molybdenum, more preferably 0 to 1.0 mol. When the amount of ammonium radical is set in this range, a catalyst with a high yield of methacrylic acid can be obtained. The amount of ammonium radical contained in the liquid I can be adjusted by the used amount of compounds containing the ammonium radical or ammonia.

As a raw material to be used in preparing the liquid I, oxides, nitrates, carbonates, ammonium salts and the like of each aforementioned element can be exemplified. The raw material can be properly selected among these compounds and used in the preparation of the liquid I.

For example, as a compound of molybdenum, a compound which doesn't contain ammonium such as molybdenum trioxide, molybdic acid or the like is preferable, however, ammonium molybdates such as ammonium paramolybdate, ammonium dimolybdate, ammonium tetramolybdate or the like can be used if a small amount of them is used. As a compound of phosphorus, orthophosphoric acid, phosphorus pentoxide, ammonium phosphate or the like can be used. As a compound of vanadium, vanadium pentoxide, ammonium metavanadate or the like can be used. Further, as a compound of phosphorus, molybdenum and vanadium, heteropolyacid such as phosphomolybdic acid, phosphovanadomolybdic acid, ammonium phosphomolybdate or the like can be used.

For each element, these compounds may be used alone or in combination of two or more kinds.

As a solvent which can be used in preparing the liquid I, for example, water, ethyl alcohol and acetone can be exemplified, however, water is preferably used. The amount of the solvent in the liquid I is not particularly limited, however, usually the content ratio (mass ratio) of the molybdenum compound to the solvent contained in the liquid I is preferably 1:0.1 to 1:100, more preferably 1:0.5 to 1:50. When the amount of the solvent is set in this range, a catalyst with a high yield of methacrylic acid can be obtained.

The liquid I can be prepared by mixing the aforementioned compound to be used as a raw material and the solvent, and stirring the resultant mixture at an ordinary temperature to dissolve or suspend the compound to make a solution or slurry. Generally, the stirring is preferably performed while heating. Usually, the heating temperature is preferably 80° C. or more, more preferably 90° C. or more. Further, the heating temperature is, usually, preferably 150° C. or less, more preferably 130° C. or less. When the heating temperature is set in this range, a catalyst with a high activity can be obtained. The heating time is, usually, preferably 0.5 hour or more, more preferably 1 hour or more. The heating time is, usually, preferably 24 hours or less, more preferably 12 hours or less. When the heating time is set in this range, the aforementioned compound can be easily dissolved or suspended, thereby the reaction among the raw materials can be sufficiently promoted.

Further, a compound of the aforementioned element Z is preferably mixed with the solvent and dissolved or suspended to prepare a solution or slurry (in some cases expressed as liquid III), and the resultant solution or slurry is preferably added to a solution or slurry containing molybdenum, phosphorus and vanadium. At this time, the temperature of the solution or slurry is preferably 80° C. or less, more preferably 30 to 70° C. As the element Z, cesium is preferable because an especially superior effect can be obtained. Foe example, as a cesium compound to be used as a raw material in the preparation of the liquid I, cesium nitrate, cesium carbonate, cesium hydroxide or the like can be used. As the cesium compound, these compounds may be used alone or in combination of two or more kinds.

<Preparing Method of the Liquid II>

The liquid II can be prepared by dissolving or suspending compounds containing ammonium radical in the solvent.

The liquid II may contain compounds of phosphorus, molybdenum, vanadium, copper, the aforementioned element X, the aforementioned element Y, and the aforementioned element Z as well as compounds containing ammonium radical, however, it is preferable that these compounds are substantially not contained.

The amount of the ammonium radical contained in the liquid II is not particularly limited, however, it is preferably 6 mols or more per 12 mols of molybdenum contained in the liquid I, and more preferably 7 mols or more. Further, the amount of the ammonium radical contained in the liquid II is preferably 17 mols or less per 12 mols of molybdenum contained in the liquid I, and more preferably 15 mols or less. When the amount of the ammonium radical is set in this range, a catalyst with a high yield of methacrylic acid can be obtained.

An ammonium radical containing compound which can be used in preparing the liquid II is ammonia or ammonium salt. Specifically, ammonia (ammonia water), ammonium carbonate, ammonium hydrogencarbonate, ammonium nitrate or the like can be exemplified as the compound. As the ammonium radical-containing compound, these compounds may be used alone or in combination of two or more kinds.

As a solvent which can be used in preparing the liquid II, for example, water, ethyl alcohol and acetone can be exemplified, however, usually, water is preferably used. The amount of the solvent in the liquid II is not particularly limited, however, usually, the content ratio (mass ratio) of the ammonium radical-containing compound to the solvent contained in the liquid II is preferably 1:0.1 to 1:100, more preferably 1:0.5 to 1:50. When the amount of the solvent is set in this range, a catalyst with a high yield of methacrylic acid can be obtained.

The liquid II can be prepared by adding the ammonium radical-containing compound to the solvent, stirring the resultant mixture at an ordinary temperature to dissolve or suspend the compound to make a solution or slurry. The liquid can be prepared by heating the resultant mixture up to around 80° C. when it is necessary. However, in case that ammonia water itself is used as the ammonium radical-containing compound, these preparing steps are not always necessary, because water which serves as solvent is already included.

<Mixing the Liquid I and the Liquid II>

In the present invention, the liquid I and the liquid II are mixed by introducing one liquid (liquid PR) of the liquid I and the liquid II into a tank (tank A) and pouring the other liquid (liquid LA) into the tank A. In case that the liquid I or the liquid II is prepared in the tank A, the resultant liquid itself serves as the liquid PR introduced into the tank A. It is important that the liquid LA is poured on a continuous region in the surface of the liquid PR introduced into the tank A, the continuous region occupying 0.01 to 10%, more preferably 0.05 to 5% of the whole area of the surface of the liquid PR.

By pouring the liquid LA into the liquid PR and mixing both liquids in this manner a catalyst with a high yield of methacrylic acid can be obtained. It is supposed that the local pH distribution in the vicinity of the mixed portion of the liquid I and the liquid II favorably acts to form an effective crystal structure for the oxidation of methacrolein and makes it possible to obtain a catalyst with a high yield of methacrylic acid.

When the liquid LA is poured into the tank A, the liquid PR introduced into the tank A is stirred with a stirring power of preferably 0.01 to 3.5 kW/m$^3$, more preferably 0.05 to 3 kW/m$^3$. By stirring the liquid PR in the range of the aforementioned stirring power, it is supposed that an effective crystal structure for the oxidation of methacrolein is formed so that the yield of methacrylic acid of the catalyst thus obtained is improved.

Further, when the liquid LA is poured into the tank A, the liquid LA is poured from the height of preferably 0.05 to 2 m, more preferably 0.1 to 1.5 m above the surface of the liquid PR introduced into the tank A. When the liquid LA is poured from the height of 0.05 m or more above the surface of the liquid PR, the liquid PR does not contact with the pouring port of the liquid LA even in the case that the liquid PR is stirred, and when the liquid LA is poured from the height of 1.5 m or less above the surface of the liquid PR, the liquid LA is not dispersed or does not contact with the wall of the tank A. Consequently, it is supposed that an effective crystal structure for the oxidation of methacrolein is formed so that the yield of methacrylic acid of the catalyst thus obtained is improved.

In the present invention, a method of pouring the liquid LA into the tank A is not particularly limited, however, a method of pouring the liquid LA by free fall from an upper part or a side part of the tank A through a pipe connected to a tank containing the liquid LA, or a method of quantitatively sending the liquid with pump and the like can be exemplified.

Number of the pouring port for pouring the liquid LA into the tank A is not particularly limited, and either one or a plurality of the pouring ports may be used as far as the liquid LA is poured on a continuous region in the surface of the liquid I and the liquid II introduced into the tank A. The number of the pouring port is preferably one under normal conditions.

In the present invention, it is possible to serve the aforementioned liquid I as the liquid PR and to serve the aforementioned liquid II as the liquid LA, or to serve the aforementioned liquid II as the liquid PR and to serve the aforementioned liquid I as the liquid LA. Further, the liquid LA can be divided into portions and poured separately in two or more times. The temperatures of the liquid LA and the liquid PR at the time when the liquid LA is poured are not particularly limited, and they are preferably 100° C. or less, more preferably 80° C. or less, and preferably the room temperature or more under normal conditions.

The liquid LA can be poured while stirring it.

When it is preferable, first, the mixture of the liquid I and the liquid II may be prepared without including the element Z according to the aforementioned method, and then the solution or slurry (the liquid III) containing the compound of the element Z may be added.

A introducing method of the liquid III is not particularly limited, and, for example, a method of introducing the liquid III to the mixture of the liquid I and the liquid II, a method of introducing the mixture of the liquid I and the liquid II to the liquid III, or a method of introducing the liquid III and the mixture of the liquid I and the liquid II at the same time can be adopted.

In the preparation of the solution or slurry containing a catalyst precursor comprising all the catalyst constituents, the liquid I and the liquid II (and further the liquid III when it is preferable) may be mixed under normal room temperature or under heating. The mixing temperature is preferably 100° C. or less, more preferably 80° C. or less, and preferably the room temperature or more under normal conditions. By mixing the liquid I and the liquid II (and further the liquid III when it is preferable) under such range of the liquid temperature and preparing the solution or slurry containing the catalyst precursor, a catalyst with a high activity is obtained. Usually, the mixing is performed while stirring. Further, the mixing time is not particularly limited, and determined properly.

<Drying/Calcining>

After the solution or slurry containing a catalyst precursor comprising all the catalyst constituents is obtained in this manner, the solution or slurry is dried and a dried catalyst precursor is obtained.

The drying method of the solution or slurry containing a catalyst precursor is not particularly limited, and a variety of methods can be used. For example, evaporation drying method, spray drying method, drum drying method, airborne drying method or the like can be used. Type of the dryer to be used in the drying, drying temperature, drying time and the like are not particularly limited, and different types of dried catalyst precursors for different purposes can be obtained by properly changing the drying condition.

The dried catalyst precursor thus obtained is ground when it is preferable and calcined to prepare a catalyst. The dried catalyst precursor may be molded in advance and calcined or can be calcined without molding it. Usually, it is preferable to make a molded form and calcine it to prepare a catalyst.

The molding method is not particularly limited, and a variety of dry or wet methods publicly known can be applied. A molding method in which silica and the like are used as a carrier can also be applied. Usually, a method in which carrier is not used is preferable. As a specific molding method, tablet molding, press molding, extrusion molding, granulation molding and the like are exemplified. The shape of the molded form is not particularly limited, and a cylindrical shape, a ring shape, a spherical shape and the like can be selected at request.

At the time of molding, a publicly known additive such as graphite, talc and the like may be added with a small quantity.

The dried catalyst precursor or its molded form thus obtained is calcined to prepare a catalyst for use in producing methacrylic acid. The calcining method and the calcining condition are not particularly limited, and a publicly known calcining method and a publicly known calcining condition can be applied. The optimum calcining condition is different depending on the catalyst raw material to be used, the catalyst composition, the catalyst preparing method and the like, and a normal condition of calcining under the flow of an oxygen containing-gas such as air or an inert gas is as follows: the calcining temperature is 200 to 500° C., preferably 300 to 450° C.; the calcining time is 0.5 hour or more, preferably 1 to 40 hours. Here, the inert gas means a gas which doesn't lower the reaction activity of the catalyst. As such a gas, specifically, nitrogen, carbon dioxide, helium, argon and the like can be exemplified.

<Method for Producing Methacrylic Acid>

Hereinafter, a method for producing methacrylic acid of the present invention is explained.

A method for producing methacrylic acid of the present invention is the method for producing methacrylic acid through gas-phase catalytic oxidation of methacrolein with molecular oxygen in the presence of the catalyst of the present invention obtained as mentioned above.

In the aforementioned method for producing methacrylic acid of the present invention, a raw gas including methacrolein and molecular oxygen is subjected to contact with a catalyst. The concentration of methacrolein in the raw gas can be changed in a wide range. Usually, the concentration of methacrolein is 1 to 20% by volume and preferably 3 to 10% by volume in particular. A small quantity of impurities such as low saturated aldehyde and the like may be contained in the raw gas. However, it is preferable to keep the quantity as small as possible.

As a molecular oxygen source, air is used from economical reason. A pure oxygen enriched air and the like can be used when it is preferable. The concentration of molecular oxygen in the raw gas is usually 0.4 to 4 mols, and preferably 0.5 to 3 mols per 1 mol of methacrolein in particular. The raw gas may be diluted by adding an inert gas such as nitrogen, carbon dioxide or the like. Further, the raw gas may be added with water vapor. The concentration of water vapor in the raw gas is usually 0.1 to 50% by volume, and preferably 1 to 40% by volume in particular. When the reaction is carried out in the presence of water vapor, methacrylic acid can be obtained with a higher yield.

The gas-phase catalytic oxidation of methacrolein is usually carried out in a fixed-bed. The number of the catalyst layer may be one, or two or more. The catalyst may be supported on a carrier or mixed with the other additives. The reaction pressure is preferably from ordinary pressure to several atmospheric pressures. The reaction temperature is usually selected in the range of from 230 to 450° C., and is preferably 250 to 400° C. in particular. The flow rate of the raw gas is not particularly limited, and usually the flow rate expressed in terms of contact time is 1.5 to 15 seconds, preferably 2 to 5 seconds.

The mechanism related to the improvement of the catalyst performance in the method for producing methacrylic acid of the present invention is not fully elucidated, however, as mentioned above, it is supposed that the local pH distribution in the vicinity of the mixed portion of the liquid I and the liquid II at the time of pouring the liquid LA into the liquid PR favorably acts to form an effective crystal structure for the oxidation of methacrolein and makes it possible to form a crystal structure with a high yield of methacrylic acid.

EXAMPLES

Hereinafter, the present invention will be entered into details with reference to the following examples and comparative examples. However, the present invention is not limited to these examples.

The catalyst composition was determined from the charged amount of the catalyst raw materials. Further, the analysis of the raw gas and the reaction products in the production of methacrylic acid was carried out using gas chromatography. Based on the analytical results obtained, the conversion of methacrolein (may be expressed as MAL conversion), the selectivity to produced methacrylic acid (may be expressed as MAA selectivity) and the single current yield of methacrylic acid (may be expressed as MAA yield) were determined by the following formulae, respectively.

The conversion of methacrolein (%)=$(B/A) \times 100$

The selectivity to methacrylic acid (%)=$(C/B) \times 100$

The single current yield of methacrylic acid (%)=$(C/A) \times 100$

In these formulae, A is a number of mol(s) of the supplied methacrolein, B is a number of mol(s) of the reacted methacrolein and C is a number of mol(s) of the produced methacrylic acid.

Further, the percentage of the area ($S_1$) of the liquid surface region on which the liquid LA was poured to the whole area of the surface of the liquid PR (may be expressed as Sp), was determined by the following formula. The whole area of the surface of the liquid PR (Sp) is a horizontal cross section inside the tank A at the height of the surface of the liquid PR, and the area ($S_1$) of the liquid surface region on which the liquid LA was poured was a horizontal cross section of the poured liquid LA at the height of the surface of the liquid PR. Further, in the examples, $S_1$ was determined as the aperture area of the pouring port because the liquid LA was poured in the liquid PR with the same size of the aperture area of the pouring port.

The percentage of the area of the surface region on which the liquid LA was poured to the whole area of the surface of the liquid PR (%)=($S_1$/Sp)×100

Example 1

To a vessel type reactor (tank A) with a diameter of 340 mm and an internal volume of 30 L, 10 kg of pure water having a room temperature was introduced and a solution obtained by dissolving 5000 g of molybdenum trioxide, 366.5 g of 85 mass % phosphoric acid, 202.8 g of ammonium methavanadate, 69.8 g of copper nitrate in 610 g of pure water and a solution obtained by dissolving 58.4 g of ferric nitrate in 250 g of pure water were added while stirring with a one-stage paddle blade and the resultant mixture was heated to 98° C. and kept at 98° C. for 5 hours while stirring. The resultant mixture was cooled to 50° C. and a solution obtained by dissolving 732.3 g of cesium in 1250 g of pure water was added to make a mixed liquid which is served as liquid I.

On the other hand, 1988 g of 25 mass % ammonia water was introduced to a reactor (tank B) with an internal volume of 2 L at room temperature to make liquid II.

The liquid I which was kept at 50° C. in the tank A and served as liquid PR was stirred with a stirring power of 0.2 kW/m$^3$ and the liquid II served as liquid LA was poured in the liquid PR from a pouring port of 20 mm in diameter at the height of 0.3 m above the surface of the liquid PR to obtain a slurry containing a catalyst precursor. The liquid surface region on which the liquid LA was poured was a continuous region with an almost circular shape having a diameter of around 20 mm and the percentage of the area of the aforementioned liquid surface region on which the liquid LA was poured to the whole area of the surface of the liquid PR was 0.4%.

The resultant slurry containing the catalyst precursor was heated to 110° C. and evaporated and dried while stirring. The resultant solid material was dried at 130° C. for 16 hours and dried material was obtained. The resultant dried material was press molded and calcined at 380° C. for 12 hours under airflow to obtain a catalyst. The composition of the catalyst thus obtained was $P_{1.1}Mo_{12}V_{0.6}Cu_{0.1}Fe_{0.05}Cs_{1.3}$.

<Reaction for Synthesizing Methacrylic Acid>

The resultant catalyst was packed in a reaction tube and a mixed gas containing 5% by volume of methacrolein, 10% by volume of oxygen, 30% by volume of water vapor and 55% by volume of nitrogen was flowed and the reaction was carried out under an ordinary pressure, at a reaction temperature of 290° C., with a contact time of 3.6 seconds. The results are shown in Table 1.

Example 2

The preparation of the catalyst and the reaction were carried out in the same manner as in Example 1 except that the liquid LA (the liquid II) was poured in the liquid PR (the liquid I) in the tank A from a pouring port of 40 mm in diameter. The results are shown in Table 1.

Example 3

The preparation of the catalyst and the reaction were carried out in the same manner as in Example 1 except that the liquid LA (the liquid II) was poured in the liquid PR (the liquid I) in the tank A from a pouring port of 100 mm in diameter. The results are shown in Table 1.

Example 4

The preparation of the catalyst and the reaction were carried out in the same manner as in Example 1 except that the liquid PR was stirred with a stirring power of 4.0 kW/m$^3$. The results are shown in Table 1.

Comparative Example 1

The preparation of the catalyst and the reaction were carried out in the same manner as in Example 1 except that the liquid LA (the liquid II) was poured in the liquid PR (the liquid I) in the tank A from a pouring port of 150 mm in diameter. The results are shown in Table 1.

Comparative Example 2

The preparation of the catalyst and the reaction were carried out in the same manner as in Example 1 except that the liquid LA was poured in the liquid PR (the liquid I) in the tank A from a pouring port of 2 mm in diameter. The results are shown in Table 1.

Comparative Example 3

The preparation of the catalyst and the reaction were carried out in the same manner as in Example 1 except that the liquid LA (the liquid II) was poured in the liquid PR (the liquid I) in the tank A from 10 pouring ports of 20 mm in diameter arranged in a ring shaped pipeline provided along the inner wall of the tank A to 10 different regions of the surface. The results are shown in Table 1.

Example 5

To a vessel type reactor (tank A) with a diameter of 650 mm and an internal volume of 250 L, 100 kg of pure water was introduced at room temperature and 50 kg of molybdenum trioxide, 2.67 kg of 85 mass % phosphoric acid, 1.84 kg of vanadium pentoxide, and 5.48 kg of 60 mass % arsenic acid aqueous solution were added while stirring with a two stage paddle blade and the resultant mixture was heated to 98° C. and kept at 98° C. for 5 hours while stirring. After 5 hours had passed, a solution obtained by dissolving 1.40 kg of copper nitrate in 6.10 kg of pure water and a solution obtained by dissolving 0.62 kg of zirconium nitrate in 3.0 kg of pure water were further added and heated and stirred for 2 hours and then cooled to 30° C. to make a mixed liquid which served as liquid I.

To a vessel type reactor (tank B) with an internal volume of 100 L, 18.1 kg of 25 mass % ammonia water was introduced at room temperature to make liquid II.

The liquid PR (the liquid I) which was kept at 30° C. in the tank A was stirred with a stirring power of 1.1 kW/m$^3$ and the liquid LA (the liquid II) was poured from a pouring port of 100 mm in diameter at the height of 1.0 m above the liquid surface in the tank A to obtain a mixed liquid of the liquid I and the liquid II. The liquid surface region of the liquid PR (the liquid I) on which the liquid LA was poured was a continuous region with an almost circular shape having a diameter of around 100 mm and the percentage of the area of the aforementioned liquid surface region on which the liquid LA was poured to the whole area of the surface of the liquid PR was 2.4%.

To the mixed liquid of the liquid I and the liquid II kept at 30° C., a solution obtained by dissolving 6.18 kg of cesium bicarbonate in 15 kg of pure water (the liquid III) was further added to obtain a slurry containing a catalyst precursor.

The resultant slurry containing the catalyst precursor was heated to 101° C. and evaporated and dried while stirring. The resultant solid material was dried at 130° C. for 16 hours. The resultant dried material was pressure molded and calcined at 380° C. for 12 hours under airflow. The composition of the catalyst thus obtained was $P_{0.8}Mo_{12}V_{0.7}Cu_{0.2}As_{0.8}Zr_{0.05}Cs_{1.1}$.

Using the catalyst, the reaction was carried out in the same manner as in Example 1. The results are shown in Table 1.

Example 6

The preparation of the catalyst and the reaction were carried out in the same manner as in Example 5 except that the liquid LA (the liquid II) was poured in the liquid PR (the liquid I) in the tank A from a pouring port at the height of 2.5 m above the liquid surface of the tank A. The results are shown in Table 1.

Comparative Example 4

The preparation of the catalyst and the reaction were carried out in the same manner as in Example 5 except that the liquid LA (the liquid II) was poured in the liquid PR (the liquid I) in the tank A from 2 pouring ports of 50 mm in diameter, each of which was arranged in the diagonal direction of 180° with respect to the total liquid surface of the tank A (interval of which was 500 mm), to 2 different almost circular regions of the surface. The results are shown in Table 1.

INDUSTRIAL APPLICABILITY

A method for producing a catalyst for use in producing methacrylic acid and the catalyst produced according to the method of the present invention can be suitably used in a method for producing methacrylic acid, including the method for producing methacrylic acid of the present invention, through gas-phase catalytic oxidation of methacrolein with molecular oxygen.

What is claimed is:

1. A method for producing a catalyst having a composition represented by the following formula (1) for use in producing methacrylic acid through gas-phase catalytic oxidation of methacrolein with molecular oxygen, comprising:
   (i) preparing a solution or slurry comprising at least molybdenum, phosphorus, and vanadium (liquid I);
   (ii) preparing a solution or slurry containing ammonium radical (liquid II);
   (iii) preparing a mixture of the liquid I and the liquid II by:
      introducing one of the liquid I and the liquid II (liquid PR) into a tank (tank A),
      subsequently pouring the other of the liquid I and the liquid II (liquid LA) into the tank already containing the liquid PR,
      the liquid LA is poured into the tank A so that when the liquid LA contacts the liquid PR the contact occurs at a continuous region on a surface of the liquid PR, and the continuous region comprises 0.01 to 10% of an entire surface area of the liquid PR in the tank A; and
   (iv) drying and calcining the resultant solution or slurry containing a catalyst precursor comprising all the catalyst constituents, $$P_aMo_bV_cCu_dX_eY_fZ_gO_h \quad (1)$$

wherein:

P, Mo, V, Cu and O represent phosphorous, molybdenum, vanadium, copper and oxygen, respectively;

X represents at least one element selected from the group consisting of antimony, bismuth, arsenic, germanium, zirconium, tellurium, silver, selenium, silicon, tungsten and boron;

TABLE 1

| | The percentage of the area of the liquid surface region on which the liquid LA was poured (%) | The shape of the area of the liquid surface region on which the liquid LA was poured | Stirring power (kW/m³) | The height at which the liquid LA was poured (m) | MAL conversion (%) | MAA selectivity (%) | MAA yield (%) |
|---|---|---|---|---|---|---|---|
| Example 1 | 0.4 | continuous | 0.2 | 0.3 | 83.1 | 86.7 | 72.0 |
| Example 2 | 1.4 | continuous | 0.2 | 0.3 | 82.8 | 87.0 | 72.0 |
| Example 3 | 8.7 | continuous | 0.2 | 0.3 | 80.4 | 87.2 | 70.1 |
| Example 4 | 0.4 | continuous | 4.0 | 0.3 | 78.8 | 87.0 | 68.6 |
| Comparative Example 1 | 19.5 | continuous | 0.2 | 0.3 | 76.5 | 86.3 | 66.0 |
| Comparative Example 2 | 0.001 | continuous | 0.2 | 0.3 | 76.0 | 86.5 | 65.7 |
| Comparative Example 3 | 3.5 | discontinuous | 0.2 | 0.3 | 79.6 | 85.4 | 68.0 |
| Example 5 | 2.4 | continuous | 1.1 | 1.0 | 81.4 | 88.3 | 71.9 |
| Example 6 | 2.4 | continuous | 1.1 | 2.5 | 80.5 | 87.5 | 70.4 |
| Comparative Example 4 | 1.2 | discontinuous | 1.1 | 1.0 | 79.4 | 85.8 | 68.1 |

Y represents at least one element selected from the group consisting of iron, zinc, chromium, magnesium, tantalum, cobalt, manganese, barium, gallium, cerium and lanthanum;

Z represents at least one element selected from the group consisting of potassium, rubidium and cesium;

subscripts a, b, c, d, e, f, g and h represent an atomic ratio of each element, respectively; and when b is 12, a is in the range of from 0.5 to 3, c is in the range of from 0.01 to 3, d is in the range of from 0.01 to 2, e is in the range of from 0 to 3, f is in the range of from 0 to 3, g is in the range of from 0.01 to 3 and h represents the atomic ratio of oxygen necessary for fulfilling the requirement of the valence of each element above.

2. The method according to claim 1, wherein the liquid LA is poured while stirring the liquid PR introduced into the tank A with a stirring power of 0.01 to 3.5 kW/m$^3$.

3. The method according to claim 1, wherein the liquid LA is poured from a height of 0.05 to 2 m above the surface of the liquid PR introduced into the tank A.

* * * * *